United States Patent [19]

Marino et al.

[11] 4,096,433
[45] Jun. 20, 1978

[54] AUTOMATIC INSPECTION FOR THE DEPOSITION OF CONDUCTIVE LIQUIDS

[75] Inventors: Louis F. Marino, Teaneck; Paul P. Monteleone, Sparta; James Remer, Matawan, all of N.J.

[73] Assignee: The United States of America as represented by the Scretary of the Army, Washington, D.C.

[21] Appl. No.: 719,553

[22] Filed: Sep. 1, 1976

[51] Int. Cl.² .................................. G01N 27/42
[52] U.S. Cl. ........................ 324/30 R; 324/71 CP; 184/1 C
[58] Field of Search ............... 324/61 R, 65 R, 65 P, 324/71 CP, 29, 30 R, 30 B; 73/194 E; 340/244 C, 269, 270; 204/129.2; 118/9, 10; 184/1 C, 6.4

[56] References Cited

U.S. PATENT DOCUMENTS

| | | | |
|---|---|---|---|
| 2,979,444 | 4/1961 | Tileg | 204/35 R |
| 3,628,139 | 12/1971 | Huber | 324/71 CP |
| 3,793,587 | 2/1974 | Thom | 324/71 CP |

*Primary Examiner*—Rudolph V. Rolinec
*Assistant Examiner*—Michael J. Tokar
*Attorney, Agent, or Firm*—Nathan Edelberg; A. Victor Erkkila; Costa Perchem

[57] ABSTRACT

An inspection method and apparatus for the deposition of a liquid material to a part in a manufacturing process. The method utilizes electrical continuity techniques to determine actual application and also controlling the dispensed volume of material.

2 Claims, 3 Drawing Figures

AUTOMATIC INSPECTION FOR THE DEPOSITION OF CONDUCTIVE LIQUIDS

GOVERNMENTAL INTEREST

The invention described herein may be manufactured, used and licensed by or for the Government for governmental purposes without the payment to us of any royalty thereon.

BACKGROUND OF THE INVENTION

This invention relates to a method and apparatus for monitoring the application of liquid materials and more particularly the deposition of a specific amount of a liquid material on a required surface.

During the process of manufacture and assembly of various items, it is often required that liquids such as lubricants, adhesives, sealants, coatings, etc., be applied to a surface of an individual part or component. Where the application of such liquids is essential or is sufficiently critical to the item or component, it is necessary to provide assurance that the liquids have indeed been applied.

With the advent of automation of manufacture and assembly, visual inspection for the deposition of liquids is not practical nor desirable. At present, there are a number of techniques for inspecting for the deposition of liquids. These include electronically sniffing for the presence of chemical vapors, optical detection, interruption of a fluidic jet and ultrasonic intrusion detection. Each of these approaches has its own particular problems, but in general, they share the common problems of complexity, high cost, and applications of highly sophisticated technology without achieving acceptable reliability.

Accordingly, it is the object of this invention to provide automatic inspection for the deposition of material on an item or a component in a manufacturing process.

It is a further object of this invention to provide a method of controlling the volume of dispensed material.

BRIEF DESCRIPTION OF THE DRAWINGS

The specific nature of the invention as well as other objects and advantages thereof will clearly appear from a description of the preferred embodiment as shown in the accompanying drawings wherein.

In the drawings like numerals refer to corresponding parts.

DESCRIPTION OF THE INVENTION

It should be recognized that liquids are characterized by some degree of electrical conductivity. The present invention utilizes this characteristic to provide the basis of a novel and practical means for automatically monitoring the deposition and the proper volume of deposition of a liquid on an item or component.

Figure 1:
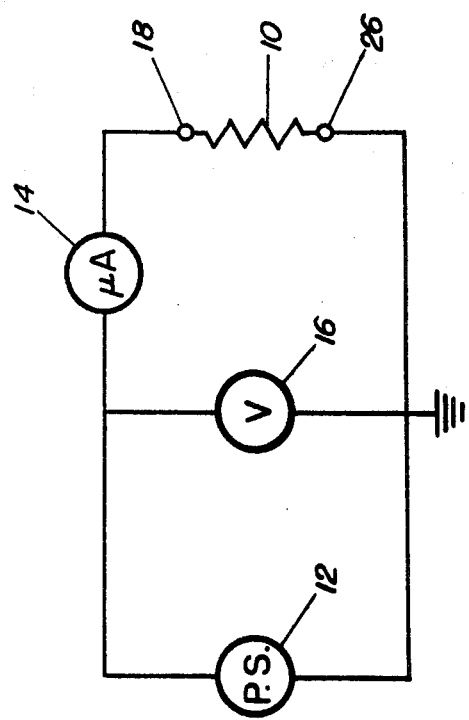
FIG. 1 is a schematic diagram of an electrical circuit utilized in the apparatus of the invention.

In the schematic diagram pictured in FIG. 1 a stream of conductive liquid, such as adhesive cement from a suitable dispenser flows onto the surface of the item to be coated. The conductive liquid 10 is modelled as a pure resistor, since any capacitive and inductive effects at low frequencies would be negligible. Connected in series is a D.C. power supply 12 and a micro-ammeter 14; the voltmeter 16 is connected in parallel.

Figure 2:
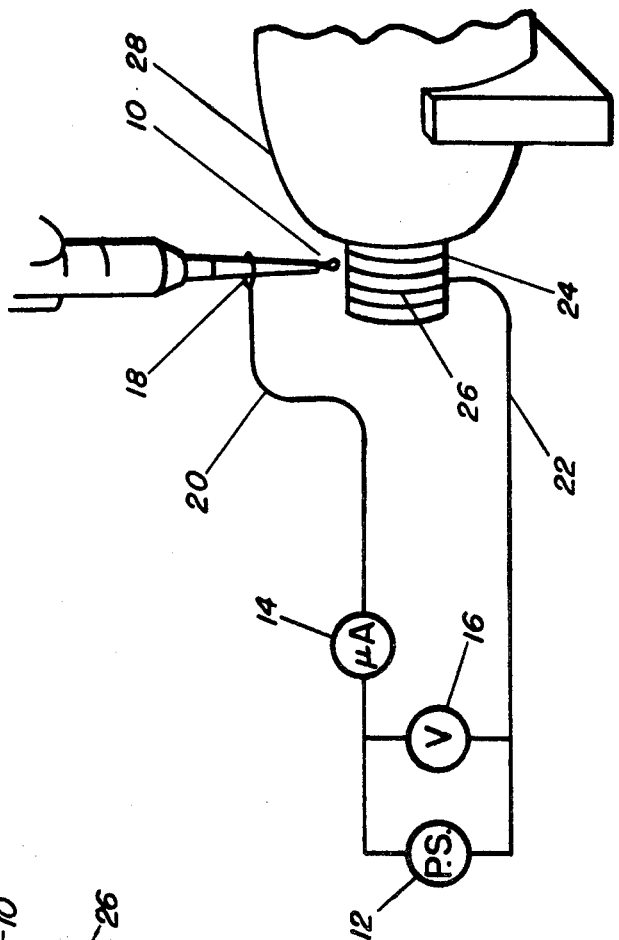
FIG. 2 shows the circuit of FIG. 1 including liquid application apparatus.

FIG. 2 is a working model of the schematic diagram shown in FIG. 1, wherein a lead 20 is provided from the micro-ammeter 14 to the needle 18 for dispensing liquid 10 and another lead 22 is provided from the power source 12 to a bare wire 26 wound on the surface 24 of the threaded end of a typical projectile 28. When the liquid 10 flows from needle 18 as an uninterrupted stream to the surface 24 it completes the circuit thereby causing a deflection of the micro-ammeter 14 which indicates that the liquid 10 is being applied to the surface 24. When the dispensing of liquid is interrupted or finished, the electrically conductive path between the needle 18 and the surface 24 is broken, and the current ceases to flow causing the micro-ammeter needle 14 to return to zero deflection. The purpose of the voltmeter 16 is employed only to facilitate adjustment of the D.C. power supply 12 while the power supply is adjusted for the differing conductivity of various fluids to be applied. Depending upon the visocity of the material, if a certain volume of liquid 10 is required to be deposited, this can be accomplished by extending the time of the deflection.

Figure 3:
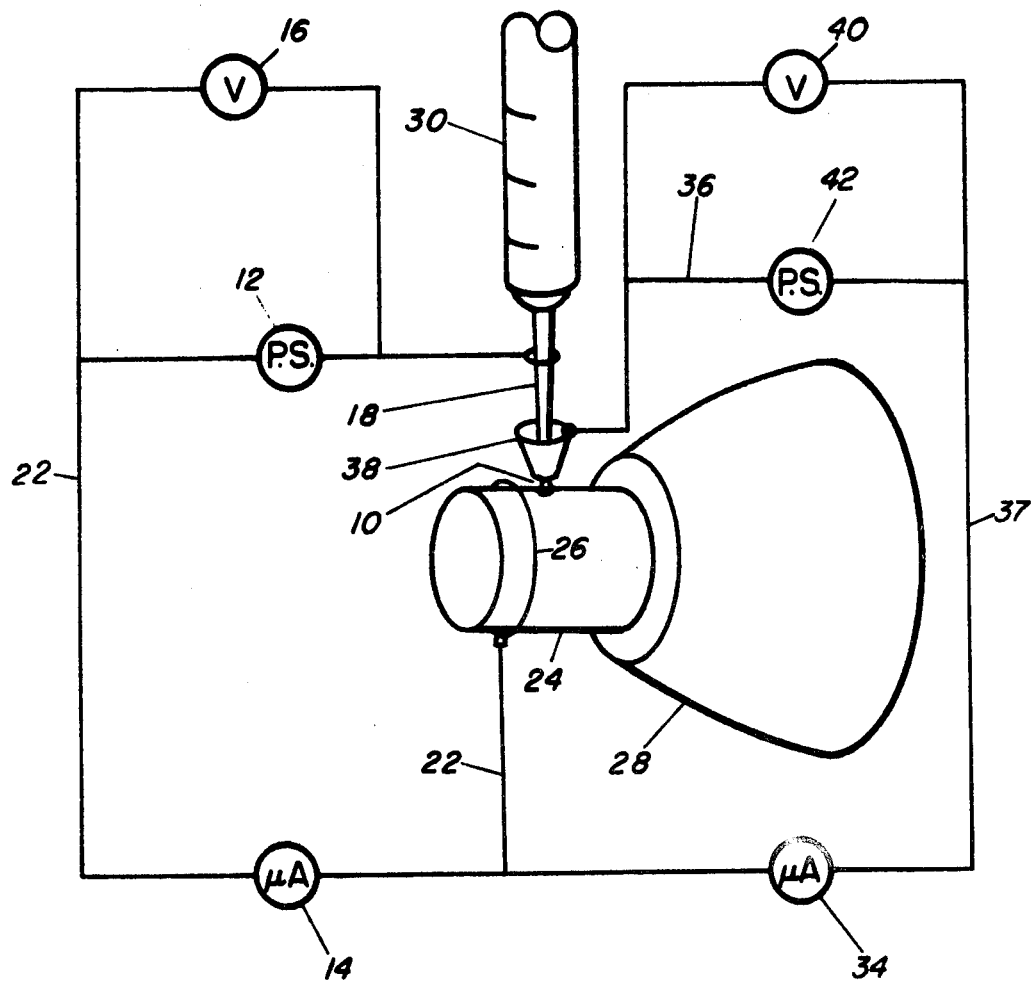
FIG. 3 is a diagram of the invention in operation.

When dealing with a highly viscous liquid, introduction of a conductive probe near the area of deposit can be employed to determine the amount of liquid deposited. The conductive probe as depicted in FIG. 3 is shown as a funnel 38. This system necessitates the addition of a second similar electrical circuit wherein the funnel 38 is connected by lead 36 to a power source 42, which in turn is connected by lead 37 containing a micro-ammeter 34 to wire 26 via lead 22. When the deposition of the highly viscous fluid builds up on the surface 24 of the threaded end of projectile 28 and comes in contact with the bottom of the funnel 38, current will flow in the second dircuit causing deflection of the micro-ammeter 34. This flow of current can serve as a signal to halt the dispensing of any additional fluid 10.

As previously noted, most liquids are characterized by some degree of conductivity. However, in a small number of liquids, the amount of conductivity is so low that the liqiud can technically be classified as an insulator. In these few instances a slight quantity of solid or liquid material, e.g. graphite, iron oxide, alcohol, is added to the fluid under inspection. This additive serves to enhance the conductivity of the liquid and thereby facilitates the inspection for the deposition of said liquid. Although a wide latitude in the choice of additive is possible, the prime consideration, aside from conductivity enhancement, should be compatability. That is, the additive should be relatively inert, and have little effect on the properties of the liquid undergoing inspection.

We wish it to be understood that we do not desire to be limited to the exact details of construction shown as described, for obvious modifications will occur to persons skilled in the art.

We claim:

1. An apparatus for inspecting for the deposition of a conductive liquid to a surface comprising:
    a reservoir containing said conductive liquid;
    a dispensing means, positioned above said surface, for applying said conductive liquid to said surface;
    a first electric circuit arranged between said dispensing means and said surface including a power source and means for measuring current flow through said circuit; whereby current can flow through said circuit only when the conductive liquid stream between said dispensing means and said surface is unbroken;
a probe means positioned above said surface for sensing the level of liquid deposited on said surface; and
a second electric circuit arranged between said probe means and said surface including a power source and means for measuring current flow through said circuit, whereby current can flow through said second circuit only when the liquid deposited on said surface contacts said probe means.

2. The apparatus as recited in claim 1, wherein said probe means is a funnel.

* * * * *